(12) United States Patent
Moroni

(10) Patent No.: US 6,426,145 B1
(45) Date of Patent: Jul. 30, 2002

(54) RADIOPAQUE COMPOSITIONS FOR VISUALIZATION OF MEDICAL DEVICES

(75) Inventor: Antonio Moroni, Morris Plains, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/569,121

(22) Filed: May 11, 2000

Related U.S. Application Data

(60) Provisional application No. 60/135,032, filed on May 20, 1999.

(51) Int. Cl.[7] ............................ B32B 27/36; A61K 49/00
(52) U.S. Cl. ................. 428/412; 428/423.1; 428/474.4; 428/480; 428/500; 424/4; 424/5; 424/9; 424/9.4
(58) Field of Search ..................... 424/4, 5, 9, 9.4; 428/412, 423.1, 474.4, 480, 500

(56) References Cited

U.S. PATENT DOCUMENTS

| | | | |
|---|---|---|---|
| 3,361,700 A | 1/1968 | Archer et al. ............... 424/9.45 |
| 3,637,394 A | 1/1972 | Smith et al. ................ 430/627 |
| 3,645,955 A | 2/1972 | Flynn ......................... 523/112 |
| 3,670,048 A | 6/1972 | Maget et al. .............. 8/115.52 |
| 3,715,331 A | 2/1973 | Molnar ...................... 523/117 |
| 4,175,544 A | 11/1979 | Newton ..................... 424/9.45 |
| 4,250,072 A | 2/1981 | Flynn ......................... 524/288 |
| 4,282,876 A | 8/1981 | Flynn ......................... 604/529 |
| 4,283,447 A | 8/1981 | Flynn ......................... 428/36.9 |
| 4,406,878 A | * 9/1983 | DeBoer |
| 4,579,879 A | 4/1986 | Flynn ......................... 523/112 |
| 4,581,390 A | 4/1986 | Flynn ......................... 523/112 |
| 4,584,326 A | 4/1986 | Flynn ......................... 523/112 |
| 5,019,370 A | 5/1991 | Jay et al. ................... 424/9.44 |
| 5,024,232 A | 6/1991 | Smid et al. ................. 600/431 |
| 5,141,739 A | 8/1992 | Jung et al. ................. 424/9.43 |
| 5,213,580 A | 5/1993 | Slepian et al. ............. 128/898 |
| 5,238,714 A | 8/1993 | Wallace et al. ........ 427/213.36 |
| 5,271,923 A | 12/1993 | Kochi et al. .............. 424/9.451 |
| 5,298,262 A | 3/1994 | Na et al. .................... 424/489 |
| 5,312,615 A | 5/1994 | Schneider et al. ........ 424/9.454 |
| 5,319,059 A | 6/1994 | Neuenschwander et al. .. 528/73 |
| 5,342,605 A | 8/1994 | Illig ........................... 424/9.43 |
| 5,368,837 A | 11/1994 | Baker et al. ............... 424/9.45 |
| 5,445,810 A | 8/1995 | Schneider et al. ........... 424/9.4 |
| 5,455,158 A | 10/1995 | Vogel et al. ................ 435/7.21 |
| 5,484,584 A | 1/1996 | Wallace et al. ............ 424/1.29 |
| 5,496,581 A | 3/1996 | Yianni et al. .............. 427/2.12 |
| 5,498,421 A | 3/1996 | Grifstaff et al. ............ 424/450 |
| 5,514,379 A | 5/1996 | Weissleder et al. ......... 424/426 |
| 5,534,250 A | 7/1996 | Klaveness et al. ....... 424/78.37 |
| 5,536,490 A | 7/1996 | Klaveness et al. ......... 424/9.52 |
| 5,541,287 A | 7/1996 | Yau et al. ................... 530/317 |
| 5,558,857 A | 9/1996 | Klaveness et al. ......... 424/9.52 |
| 5,562,099 A | 10/1996 | Cohen et al. ............... 600/458 |
| 5,565,215 A | 10/1996 | Gref et al. .................. 424/501 |
| 5,567,410 A | 10/1996 | Torchilin et al. ............ 424/9.4 |
| 5,569,449 A | 10/1996 | Klaveness et al. ......... 424/9.51 |
| 5,607,660 A | 3/1997 | Lee et al. .................... 424/9.4 |
| 5,616,312 A | 4/1997 | Rosik ....................... 424/9.364 |
| 6,048,362 A | 4/2000 | Berg ......................... 623/1.34 |

FOREIGN PATENT DOCUMENTS

| | | |
|---|---|---|
| EP | 0 203 833 A1 | 12/1986 |
| EP | 0 452 123 A1 | 10/1991 |
| WO | WO82/01006 | 4/1982 |
| WO | WO88/06162 | 8/1988 |

\* cited by examiner

*Primary Examiner*—Leszek Kiliman
(74) *Attorney, Agent, or Firm*—Hoffmann & Baron, LLP

(57) ABSTRACT

A radiopaque polymeric composition useful as a polymer coating on a substrate. The compositions are designed to be bioabsorbable and are particularly useful on implantable medical devices, such as vascular prostheses and the like.

24 Claims, No Drawings

RADIOPAQUE COMPOSITIONS FOR VISUALIZATION OF MEDICAL DEVICES

"This application claims the benefit of U.S. Provisional Application No. 60/135,032, filed on May 20, 1999."

FIELD OF THE INVENTION

The present invention relates to polymeric radiopaque materials. More particularly, the present invention relates to biocompatible and biostable radiopaque coatings useful in conjunction with implantable medical devices.

BACKGROUND OF THE INVENTION

Medical radiography is a well known and important method used for early detection and diagnosis of various disease states of the human body. However, most implantable and non-implantable surgical devices exhibit little absorption of x-ray radiation so that radiographs of both the devices and their environs are difficult to obtain. The ability to see the radiographic image of a medical device being used in or implanted within the body is very important. For example, an implanted medical device, such as an endovascular prosthesis, may need adjustment and monitoring both d ring and after implantation in the body. Radiographic imaging provides the surgeon with the ability to properly perform such adjustments. Additionally, minimally invasive procedures, which are now very commonplace, require monitoring via radiographic imaging to guide the physician. Devices such as catheters which are not intended to be left for any length of time in the body may employ conventional radiopaque metal markers which are usually disposed at the distal end to indicate the catheter whereabouts in the vessel. Such radiopaque markers are not useful, however, in implantable devices which are required to be porous and flexible, such as vascular prosthesis. Vascular grafts, including those which are surgically implanted arid those which are introduced intraluminally, are designed to mimic the natural vessels and hence require a unique combination of features to be present. The graft must be sufficiently porous to allow cellular ingrowth and encapsulation by the body, yet be fluid-tight to prevent leakage of blood. Additionally, flexibility and compliance are also key features of a successful graft product. Thus, use of metal bands or conventional radiopaque markers are unacceptable in such devices. Moreover, if a radiopaque composition is to be applied as a coating over the graft, it must permit the natural process of cellular ingrowth to occur within the first few weeks of being implanted.

To overcome this problem a variety of conventional approaches have been developed, and numerous patents disclose radiopaque compounds or polymers used in the body.

Radiographic techniques have included the injection of micro-encapsulated particles into the patient which release a radiopaque agent into the body to aid X-ray analysis of tissue and organs which are not otherwise visible by X-rays. For example, U.S. Pat. No. 5,342,605 discloses an X-ray contrast composition for oral or retrograde examination of the gastrointestinal tract comprising a divalent cation capable of forming a coating on the tract, and an iodinated radiopaque agent. Gref, et al., U.S. Pat. No. 5,565,215 discloses an injectable microparticle for the controlled release of substances for diagnostic imaging that can optionally be targeted to specific organs or cells. While these techniques may be useful for radioscopy of the gastrointestinal tract and target organs, they do not provide adequate means to detect and monitor medical devices inserted into the body which are otherwise transparent to X-ray imaging. Moreover, these radiopaque agents are not useful as biostable materials which can be used as polymeric coatings on implantable medical devices such as vascular grafts.

Furthermore, a number of patents disclose polymeric tubing which includes radiopaque polymer. U.S. Pat. No. 3,361,700 discloses a family of alkoxyalkyl esters of diiodobenzoic acid that are radiopaque and suitable to plasticize vinyl resins into a form useful for the manufacture of tubings for catheters and similar products. U.S. Pat. No. 3,645,955 discloses that di- and tetraiodoesters are superior for this purpose because they show less tendency to exude from the polymer tubing and can be used in lower concentrations, thereby providing a better balance between, flexibility and stiffness of the polymer article. While these compositions are quite suitable for the production of tubing of simple types, they are not completely satisfactory for production of more complicated shaped devices, as they have problems retaining more complex shapes. U.S. Pat. Nos. 4,250,072, and 4,283,447 disclose that if the vinyl resin is replaced partially or completely by thermoplastic polyurethane, the iodoester radiopacified compositions are amenable to the induction of complex shapes, i.e., they retain their shape. U.S. Pat. No. 4,579,879 discloses employing a controlled amount of platinum-cured silicon network polymers in such tubing to provide a surface which is more hydrophobic and gives a longer service life.

Neuenschwander, et al., U.S. Pat. No. 5,319,059 disclose a biocompatible X-ray contrasting composition:wherein the X-ray contrast material is covalently attached to a polyurethane matrix. However, the polyurethane matrix is unstable, and may be reabsorbed into the body, rendering the article invisible by radiographic imaging. This may be problematic for applications to implantable articles, whose presence would become undetectable to x-rays after decomposition of the x-ray contrast material.

Larsen, European Patent Publication No. 0 203 833, discloses a composition comprising a x-ray contrasting thermoset polymer comprised of a crosslinkable polyester resin which is dissolved in a vinyl monomer. This composition may be used to manufacture surgical articles. It However, due to the solid polymer's inflexibility it may not be used to create flexible devices and would certainly be inappropriate to use as any time of prosthetic implant which required flexibility.

Thus, while the prior art has suggested various radiopaque compounds and additives to compositions which are useful in the body, there has yet to be developed a safe, biostable polymeric coating which is easy to apply to the surface of flexible, porous medical devices, such as a vascular graft, and which forms a stable coating. Thus, there is a definite need for a radiopaque polymeric composition which can be particularly useful as a coating for medical devices, and particularly implantable medical devices, and is biocompatible and biostable.

Therefore, it is, an object of the present invention to provide such a polymeric radiopaque composition. In particular, the inventive composition is capable of adhering to or becoming part of a substrate, and capable of forming a flexible film. Furthermore, the inventive composition also possesses an appropriate amount of tackiness, crystallinity and lubricity for use as a medical device coating. Such properties can be obtained in the inventive compositions by tailoring the molecular structure in the polymer groups attached to the radiopaque components.

The present invention may be applied as a coating to a medical device or may become part of the polymer matrix used to form the device, in either case serving to provide radiopaque character to the device and thus making the device visible by X-ray imaging techniques.

Furthermore, the present invention utilizes a polymeric composition which displays improved physical properties over prior radiopaque compositions and forms a coating which has a wide adaptable range of physical properties including tackiness, lubricity, hemocompatibility, cell compatibility, and flexibility. The physical characteristics of the polymer are especially important when it is employed on vascular grafts which require natural tissue ingrowth for assimilation into the body. The polymeric radiopaque composition may be tailored to provide a substrate surface which allows the necessary neointimal ingrowth and renders the graft radiopaque, while also maintaining the graft's flexibility.

SUMMARY OF THE INVENTION

The present invention includes a radiopaque polymeric composition having the formula:

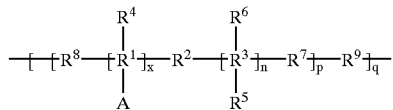

wherein A is a substituted or unsubstituted aromatic or aliphatic group containing a radiopaque component and at least one functional group, said functional group being capable of forming a linkage with $R^1$ and is selected from the group consisting of carboxyl, amino, hydroxyl, isocyanato, and halo. $R^1$ and $R^3$ are substituted or unsubstituted aliphatic or aromatic groups having from 1 to 20 carbons, and having at least two reactive ends being the same or different, said reactive ends being selected from the group consisting of carboxyl, amino, hydroxyl, isocyanato, and halo. X is an integer from 1 to 1,000. N is an integer from 0 to 1,000, provided that when n is zero $R^7$ is absent. $R^2$, $R^7$ and $R^8$ may be optionally present, and may be the same or different, substituted or unsubstituted groups selected from the difunctional groups consisting of diols, diamines, hydroxy acids and amino acids. $R^4$, $R^5$, and $R^6$ may be the same or different substituents selected from the group consisting of hydrogen, halogen or a hydrocarbon chain having from 1 to 100 carbons. $R^9$ is an optional chain extender containing at least two end groups being the same or different and selected from the group consisting of amino, hydroxyl, icocyanate, carbonate, anhydride, acyl chloride, and carboxyl. P is an integer from 1 to 100, and q is an integer from 1 to 100.

DETAILED DESCRIPTION OF THE INVENTION

The following is a detailed description of the present invention. The description is meant to describe the preferred embodiments, and is not meant to limit the invention in any way.

In a preferred embodiment of the present invention the carbon groups of $R^1$ and $R^3$ may be polyester, polyether, polycarbonate, polyamide, or a polyester polyamide copolymer. Polyester is an especially desirous group to attach to the aromatic component because of several advantageous physical properties it imparts.

The radiopaque polymeric compositions of the present invention need not be cross-linked to perform effectively. The physical properties of the inventive compositions make them very suitable for use as coatings on medical devices. Furthermore, certain portions of the polymeric compositions, i.e., groups $R^4$, $R^5$, and $R^6$ may be varied, and depending on the choice of substituents, the composition's properties of adhesion, crystallinity, tackiness, lubricity, hemocompatibility, cell compatibility and flexibility can be controlled.

In another preferred embodiment of the present invention the radiopaque component of the invention includes an iodinated aromatic ring. In another preferred embodiment of the invention, $R^2$ of the radiopaque polymeric composition forms an ester group connected to said aromatic or aliphatic group of $R^3$. The polyester is optimally attached through the functional groups to a radiopaque component which includes an iodinated aromatic ring.

The compositions of the present invention may be applied as a coating to an implantable or a non-implantable medical device. The compositions of the present invention are suitable to coat substrates of implantable devices because they possess desirous properties of biocompatibility and biostability. Such devices may include, without limitation, catheters, stents, or grafts. A method of imparting the radiopaque polymeric composition to a surface of such a device is also disclosed.

Many of the physical properties of the radiopaque compositions of the present invention can be altered with different compositions some of the components. Specifically, $R^4$, $R^5$, and $R^6$ may be chosen from a variety of different formulations in order to impart characteristics which alter one or more of the composition's properties, said properties being selected from the group consisting of adhesion; crystallinity, tackiness, lubricity, hemocompatibility, cell compatibility, and flexibility.

The present invention also comprises a medical device having at least one radiopaque surface, the radiopaque surface comprising a polymeric composition having the formula:

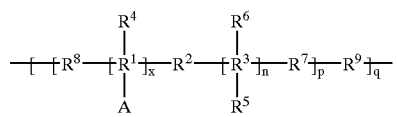

wherein A is a substituted or unsubstituted aromatic or aliphatic group containing a radiopaque component and a functional group, said functional group being capable of forming a linkage with $R^1$ and is selected from the group consisting of carboxyl, amino, hydroxyl, isocyanato, and a halo; $R^1$ and $R^3$ are substituted or unsubstituted aliphatic or aromatic groups having from 1 to 20 carbons, and having at least two reactive ends being the same or different, said reactive ends being selected from the group consisting of carboxyl, amino, hydroxyl, isocyanato, and halo; x is an integer from 1 to 1,000 and preferably from 10 to 100; and n is an integer from 0 to 1,000, and preferably from 10 to 100; provided that when n is zero $R^7$ is absent. $R^2$, $R^7$, and $R^8$ may be optionally present, and,:may be the same or different, substituted or unsubstituted groups selected from the difunctional groups consisting of diols, diamines, hydroxy acids, and amino acids. $R^4$, $R^5$, and $R^6$ may be the same or different substituents selected from the group consisting of hydrogen, halogen, or a hydrocarbon chain having from 1 to 100 carbons. $R^9$ is an optional chain extender containing at least two end groups being the same or different and selected from the group consisting of amino, hydroxyl, isocyanato, carbonate, anhydride, acyl chloride, and carboxyl. P is an integer from 1 to 100, and q is an integer from 1 to 100.

The medical device may be a wide variety of devices, and may be implantable or non-implantable. A list of such medical devices includes, but is not limited to catheters, balloons, grafts, surgical felts, stents, nets, PTFE, or any other medical fabrics. Non-medical device uses for the present compositions include engineering, automotive and aerospace applications where diagnostic testing is used.

The present invention also describes a method of imparting a radiopaque polymeric coating of the above formula to a surface of an article by contacting said surface with the radiopaque polymeric composition listed above.

The radiopaque polymeric composition may be applied to a medical device or other article in a variety of ways, including dipping, steeping, or spraying the coating on to the article. A number of layers may be imparted onto the device or article, ranging from 1 to 10 number of layers. In order to apply the polymer to a substrate, the polymeric composition should have a viscosity in a suitable range where it is low enough that it can be sprayed or applied, and high enough to ensure proper application with no problems with adhering the polymeric composition to the substrate.

The radiopaque polymeric coatings of the present invention may be prepared by a variety of chemical reaction routes. The compositions of the present invention may be formed by condensation reactions but is not limited by this type of reaction.

What is claimed is:

1. A radiopaque polymeric composition having the formula

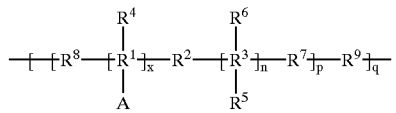

wherein A is a substituted or unsubstituted aromatic or aliphatic group containing a radiopaque component and a functional group, said functional group being capable of forming a linkage with $R^1$ and is selected from the group consisting of carboxyl, amino, hydroxyl, isocyanato, and a halo; $R^1$ and $R^3$ are different substituted or unsubstituted aliphatic or aromatic groups having from 1 to 20 carbons, and having at least two reactive ends being the same or different, said reactive ends being selected from the group consisting of carboxyl, amino, hydroxyl, isocyanato, and halo; x is an integer from 1 to 1,000; n is an integer from 1 to 1,000; $R^2$, $R^7$, and $R^8$ may be optionally present, and may be the same or different, substituted or unsubstituted groups selected from the difunctional groups consisting of diols, diamines, hydroxy acids, and amino acids; $R^4$, $R^5$, and $R^6$ may be the same or different substituents selected from the group consisting of hydrogen, halogen, or a hydrocarbon chain having from 1 to 100 carbons; $R^9$ is an optional chain extender containing at least two end groups being the same or different and selected from the group consisting of amino, hydroxyl, carbonate, anhydride, acyl chloride, and carboxyl; p is an integer from 1 to 100; q is an integer from 1 to 100.

2. A radiopaque polymeric composition according to claim 1 wherein the substituted or unsubstituted aromatic or aliphatic carbon groups of $R^1$ and $R^3$ are a polymeric group, said group being selected from the group consisting of polyester, polyether, polycarbonate, polyamide, or polyester polyamide copolymer.

3. A radiopaque polymeric composition according to claim 1 wherein $R^2$ forms an ester group connected to an said aromatic or aliphatic group of $R^3$.

4. A radiopaque polymeric composition according to claim 1 wherein the radiopaque component includes an iodinated aromatic ring.

5. A radiopaque polymeric composition according to claim 1 which is both biocompatible and biodegradable.

6. A radiopaque polymeric composition according to claim 1 wherein the polymeric composition is not cross linked.

7. A radiopaque polymeric composition according to claim 1 applied to the substrate of a medical device.

8. A medical device according to claim 6 wherein the medical device is implantable.

9. A radiopaque polymeric composition according to claim 1 wherein $R^4$, $R^5$ and $R^6$ are chosen to impart characteristics which alter one or more of the composition's properties, said properties being selected from the group consisting of adhesion, crystallinity, tackiness, lubricity, hemocompatibility, cell compatibility, and flexibility.

10. A medical device having at least one radiopaque surface, said radiopaque surface comprising:

a polymeric composition having the formula

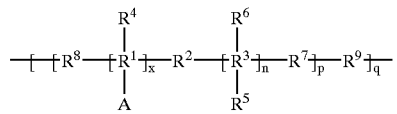

wherein A is a substituted or unsubstituted aromatic or aliphatic or aliphatic group containing a radiopaque component and a functional group, said functional group being capable of forming a linkage with $R^1$ and is selected from the group consisting of carboxyl, amino, hydroxyl, isocyanato and halo; $R^1$ and $R^3$ are different substituted or unsubstituted aliphatic or aromatic groups having from 1 to 20 carbons, and having at least two reactive ends being same or different, said reactive ends being selected from the group consisting of carboxyl, amino, hydroxyl, isocyanato, and halo; x is an integer from 1 to 1,000; n is an integer from 1 to 1,000; $R^2$, $R^7$, and $R^8$ may be optionally present, and may be the same or different, substituted or unsubstituted groups selected from the difunctional groups consisting of diols, diamines, hydroxy acids, and amino acids; $R^4$, $R^5$, and $R^6$ may be the same or different substituents selected from the group consisting of hydrogen, halogen, or a hydrocarbon chain having from 1 to 100 carbons; $R^9$ is an optional chain extender containing at least two end groups being the same or different and selected from the group consisting of amino, hydroxyl, carbonate, anhydride, acyl chloride, and carboxyl; p is an integer from 1 to 100; q is an integer from 1 to 100.

11. A medical device according to claim 10 wherein $R^1$ and $R^3$ of the polymeric composition which comprises the radiopaque surfaces are a polymeric group, said group being selected from the group consisting of polyester, polyether, polycarbonate, polyamide, or polyester polyamide copolymer.

12. A medical device according to claim 10 wherein the polymeric composition which comprises the radiopaque surface includes an iodinated ring.

13. A medical device according to claim 10 wherein the polymeric composition which comprises the radiopaque surface is both biocompatible and biodegradable.

14. A medical device according to claim 10 wherein the polymeric composition which comprises the radiopaque surface is not cross linked.

15. A medical device according to claim 10 wherein such device is a graft.

16. A medical device according to claim 10 wherein such device is a stent.

17. A medical device according to claim 10 wherein such device is a catherer.

18. A method of imparting a radiopaque polymeric coating to a surface of an article which comprises:

a) contacting said surface with a radiopaque polymeric composition, said composition having the following formula:

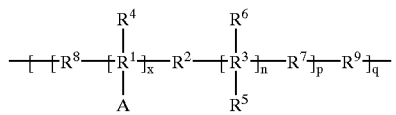

wherein A is a substituted or unsubstituted aromatic or aliphatic group containing a radiopaque component and a functional group, said functional group being capable of forming a linkage with $R^1$ and is selected from the group consisting of carboxyl, amino, hydroxyl, isocyanato, and halo;

$R^1$ and $R^3$ are different substituted or unsubstituted aliphatic or aromatic groups having from 1 to 20 carbons, and having at least two reactive ends being the same or different, said reactive ends being selected from the group consisting of carboxyl, amino, hydroxyl, isocyanato, and halo; x is an integer from 1 to 1,000; n is an integer from 1 to 1,000; $R^2$, $R^7$, and $R^8$ may be optionally present, and may be the same or different, substituted or unsubstituted groups selected from the difunctional groups consisting of diols, diamines, hydroxy acids, and amino acids; $R^4$, $R^5$, and $R^6$ may be the same or different substituents selected from the group consisting of hydrogen, halogen, or a hydrocarbon chain having from 1 to 100 carbons; $R^9$ is an optional chain extender containing at least two end groups being the same or different and selected from the group consisting of amino, hydroxyl, carbonate, anhydride, acyl chloride, and carboxyl; p is an integer from 1 to 100; q is an integer from 1 to 100.

19. The method of claim 18 wherein said article is a medical device.

20. The method of claim 18 wherein said article is a graft.

21. The method of claim 18 wherein said article is a stent.

22. The method of claim 18 wherein said article is a catherer.

23. The method of claim 18 wherein said contacting is by dipping, brushing or spraying.

24. The method of claim 18 wherein said contacting further comprises applying from about 0 to 100 layers of the radiopaque polymeric composition to the surface of said article.

* * * * *